(12) United States Patent
Straw et al.

(10) Patent No.: US 11,505,777 B2
(45) Date of Patent: Nov. 22, 2022

(54) BIOLOGICAL PROCESSING ASSEMBLY

(71) Applicant: EXTRACT TECHNOLOGY LIMITED, Huddersfield (GB)

(72) Inventors: David Straw, Holmfirth (GB); Matthew James Pridden, Doncaster (GB); Daryl Lister, Huddersfield (GB); Richard Michael Auty, Barnsley (GB); Stephen Mark Carpmail, Warrington (GB); Daniel James Ferguson, Huddersfield (GB); Paul Nigel Hudson, Mirfield (GB)

(73) Assignee: EXTRACT TECHNOLOGY LIMITED, Huddersfield (GB)

( * ) Notice: Subject to any disclaimer, the term of this patent is extended or adjusted under 35 U.S.C. 154(b) by 123 days.

(21) Appl. No.: 16/645,141

(22) PCT Filed: Sep. 17, 2018

(86) PCT No.: PCT/GB2018/052647
§ 371 (c)(1),
(2) Date: Mar. 6, 2020

(87) PCT Pub. No.: WO2019/058104
PCT Pub. Date: Mar. 28, 2019

(65) Prior Publication Data
US 2021/0179999 A1  Jun. 17, 2021

(30) Foreign Application Priority Data
Sep. 20, 2017  (GB) .................................... 1715168

(51) Int. Cl.
*C12M 3/00* (2006.01)
*C12M 1/00* (2006.01)
*B01L 1/02* (2006.01)

(52) U.S. Cl.
CPC .............. *C12M 41/14* (2013.01); *B01L 1/02* (2013.01); *C12M 23/44* (2013.01); *C12M 23/48* (2013.01);
(Continued)

(58) Field of Classification Search
CPC ...... C12M 41/14; C12M 23/48; C12M 23/44; B01L 1/02
See application file for complete search history.

(56) References Cited

U.S. PATENT DOCUMENTS 3,907,389 A   9/1975  Cox et al.
4,111,753 A   9/1978  Folsom et al.
(Continued)

FOREIGN PATENT DOCUMENTS

EP    0830896 A2    3/1998
EP    1471138 A1    10/2004
(Continued)

OTHER PUBLICATIONS

International Search Report and Written Opinion of the International Searching Authority issued in PCT/GB2018/052647, dated Dec. 11, 2018; ISA/EP.

*Primary Examiner* — Nathan A Bowers
(74) *Attorney, Agent, or Firm* — Harness, Dickey & Pierce, P.L.C.

(57) ABSTRACT

The present invention relates to a biological (eg cell) processing assembly comprising an aseptic chamber with apertures adapted for gloves to fit and an incubation chamber connectable to aseptic chamber with transfer hatches, doors secured by multi-walls and inflatable seals, stepped collars for tight closure of doors and closed interaction between the chambers. From the aseptic chamber it can be reached through into incubation chamber. There is a docking spigot on outlet wall to interact with stepped collar to define
(Continued)

transfer port between the chambers and a disinfectant delivery device to disinfect transfer port.

10 Claims, 9 Drawing Sheets

(52) U.S. Cl.
CPC ........ *C12M 23/50* (2013.01); *B01L 2200/082* (2013.01); *B01L 2200/141* (2013.01)

(56) References Cited

U.S. PATENT DOCUMENTS

| | | | | |
|---|---|---|---|---|
| 4,162,196 | A * | 7/1979 | Folsom | B01L 1/02 435/304.1 |
| 5,567,025 | A * | 10/1996 | Haag, III | B01L 1/02 220/377 |
| 6,732,424 | B2 * | 5/2004 | Nadicksbernd | B24C 3/04 118/733 |
| 6,779,567 | B1 | 8/2004 | Szatmary | |
| 9,279,099 | B2 * | 3/2016 | Okano | C12M 41/48 |
| 2018/0079999 | A1 * | 3/2018 | Blanchard | C12M 37/04 |
| 2019/0193287 | A1 * | 6/2019 | Nishimura | C12M 23/52 |
| 2019/0241851 | A1 * | 8/2019 | Valat | A61P 9/00 |

FOREIGN PATENT DOCUMENTS

| | | |
|---|---|---|
| WO | WO-0191810 A1 | 12/2001 |
| WO | WO-2007/009000 A2 | 1/2007 |
| WO | WO-2007/049078 A1 | 5/2007 |

\* cited by examiner

BIOLOGICAL PROCESSING ASSEMBLY

CROSS-REFERENCE TO RELATED APPLICATIONS

This application is a 371 U.S. National Phase of International Application No. PCT/GB2018/052647, filed Sep. 17, 2018, which claims priority to British Patent Application No. 1715168.9, filed Sep. 20, 2017. The entire disclosures of the above applications are incorporated herein by reference.

The present invention relates to a biological (eg cell) processing assembly.

Effective containment is essential for the safe and hygienic handling of biological (eg microbiological) entities such as cells, bacteria, viruses or other microorganisms (eg for clinical use). At each processing stage, handling must be controlled and managed to provide optimum protection for the operator and to maintain the integrity of the biological entities.

For handling a biological material of a sensitive or hazardous nature in a processing zone, there are available a number of different types of processing assembly. Certain conventional cell processing assemblies provide gloved access to an aseptic environment for processing biological material which may be integrated with one or more biological incubators providing an incubation environment for the biological material.

The present invention is based on the recognition that creating an isolatable port between the incubation environment and the aseptic environment enables the performance of a biological processing assembly to be improved.

Thus viewed from one aspect the present invention provides a biological processing assembly comprising:

- a multi-walled aseptic chamber which encloses an aseptic processing zone beyond an access wall thereof for processing biological material;
- an aperture within the access wall;
- a glove port fitted to the access wall at or near to the circumference of and coaxial with the aperture, wherein an exterior surface of the glove port extends into a retaining portion;
- a flexible glove retained on the retaining portion of the glove port, wherein the flexible glove is adapted or adaptable to permit an operator outside the aseptic processing zone to reach through the aperture within the access wall to access the aseptic processing zone and beyond;
- a transfer hatch within a transfer wall of the multi-walled aseptic chamber, wherein a lip of the transfer hatch extends radially and outwardly into a stepped collar;
- a transfer door mounted pivotally on the transfer wall of the multi-walled aseptic chamber, wherein in use the operator outside the aseptic processing zone reaches through the aperture within the access wall to pivot the transfer door to engage with the stepped collar so as to close the transfer hatch or to pivot the transfer door to disengage from the stepped collar so as to open the transfer hatch;
- a multi-walled incubating enclosure which encloses an incubation zone for the biological material;
- an outlet hatch within an outlet wall of the multi-walled incubating enclosure;
- a barrier door mounted pivotally on the outlet wall of the multi-walled incubating enclosure, wherein in use the operator outside the aseptic processing zone reaches through the aperture within the access wall and the transfer hatch within the transfer wall to pivot the barrier door to open or close the outlet hatch;
- a docking spigot extending outwardly from an exterior surface of the outlet wall, wherein the docking spigot skirts the outlet hatch and is dockable or docked with the stepped collar to define a transfer port between the incubation zone and the aseptic processing zone;
- a first seal mounted between the transfer door and stepped collar;
- a second seal mounted between the docking spigot and stepped collar, wherein when the transfer door and barrier door are closed the transfer port is substantially isolated; and
- a disinfectant delivery device fitted to the stepped collar whereby in use to deliver disinfectant to the transfer port.

By virtue of its isolation, the transfer port can be bio-decontaminated discretely using a disinfectant before the biological material is transferred from the incubation zone through the bio-decontaminated transfer port to the aseptic processing zone for processing.

The multi-walled incubating enclosure is equipped to carry out incubation of biological entities (eg cells) in the incubation zone.

The multi-walled incubating enclosure typically adopts a substantially cuboidal configuration (eg a box-like configuration) having a rear wall, a front wall, a basal wall, a first side wall, a second side wall and an upper wall, wherein the front wall is the outlet wall.

Preferably the multi-walled incubating enclosure is adapted for manual ground-bearing propulsion (eg adapted to be mobile). Particularly preferably the multi-walled incubating enclosure is wheeled (eg with ground-bearing casters).

By virtue of being adapted for manual ground-bearing propulsion, the multi-walled incubating enclosure is advantageously moved freely between an undocked and a docked position relative to the multi-walled aseptic chamber. The ability to manually dock and undock multiple multi-walled incubating enclosures with a multi-walled aseptic chamber gives the biological processing assembly considerable versatility and capacity (for example to carry out multi-step biological processing).

The docking spigot is typically annular (eg square annular).

The biological processing assembly may further comprise an exterior door mounted pivotally on the multi-walled incubating enclosure to the exterior of the barrier door.

The multi-walled aseptic chamber is equipped to carry out processing of biological entities (eg cells) in the aseptic processing zone.

The multi-walled aseptic chamber typically adopts a substantially cuboidal configuration (eg a box-like configuration) having a rear wall, a front wall, a basal wall, a first side wall, a second side wall and an upper wall, wherein the front wall is the access wall and the first side wall is the transfer wall.

In a preferred embodiment, the multi-walled aseptic chamber is floor-standing. For example, the basal wall may be equipped with a ground-bearing framework.

The biological processing assembly may further comprise one or more additional apertures (eg three additional apertures) within the access wall and an additional glove port fitted to the access wall at or near to the circumference of and coaxial with each additional aperture, wherein an exterior surface of the additional glove port extends into a retaining portion and an additional flexible glove is retained on the retaining portion of the additional glove port, wherein the additional flexible glove is adapted or adaptable to permit an operator outside the aseptic processing zone to reach through the additional aperture within the access wall to access the aseptic processing zone.

In a preferred embodiment, the biological processing assembly further comprises a second aperture within the access wall and a second glove port fitted to the access wall at or near to the circumference of and coaxial with the second aperture, wherein an exterior surface of the second glove port extends into a retaining portion and a second flexible glove is retained on the retaining portion of the second glove port, wherein the second flexible glove is adapted or adaptable to permit an operator outside the aseptic processing zone to reach through the second aperture within the access wall to access the aseptic processing zone.

Preferably the lip of the transfer hatch extends outwardly and radially into an innermost seat of the stepped collar, wherein in use the operator outside the aseptic processing zone reaches through the aperture within the access wall to pivot the transfer door to engage with the innermost seat of the stepped collar so as to close the transfer hatch or to pivot the transfer door to disengage from the innermost seat of the stepped collar so as to open the transfer hatch. Particularly preferably in use an outer circumferential edge of the transfer door engages the innermost seat of the stepped collar so as to close the transfer hatch and disengages from the innermost seat of the stepped collar so as to open the transfer hatch.

Preferably the innermost seat of the stepped collar extends outwardly and radially into an intermediate wall.

Preferably the intermediate wall extends outwardly and radially into an annularly recessed seat of the stepped collar, wherein the docking spigot is dockable or docked with the annularly recessed seat of the stepped collar to define the transfer port between the incubation zone and the aseptic processing zone.

Typically the annularly recessed seat of the stepped collar is outermost. The annular recess may define a substantially square cross-section.

The stepped collar is typically annular (eg square annular). The transfer door is typically substantially square.

Preferably the first seal is mounted on the transfer door. Particularly preferably the first seal is mounted in a recess in at least a part of the outer circumferential edge of the transfer door.

Preferably the second seal is mounted on the stepped collar. Particularly preferably the second seal is mounted in the annularly recessed seat of the stepped collar.

Preferably the first seal is a first inflatable seal. The inflation of the first inflatable seal may be triggered by a first proximity switch.

Preferably the second seal is a second inflatable seal. The inflation of the second inflatable seal may be triggered by a second proximity switch.

In a preferred embodiment, the first seal is a first inflatable seal and the second seal is a second inflatable seal, wherein when the transfer door and barrier door are closed and the first inflatable seal and second inflatable seal are inflated the transfer port is substantially isolated.

Preferably the biological processing assembly further comprises an inner seal mounted between the barrier door and the outlet wall. The inner seal is typically mounted on the outlet wall.

Preferably the disinfectant delivery device comprises an inlet pipe connected to a first bore in the stepped collar and an outlet pipe connected to a second bore in the stepped collar. The first bore and second bore may be in at least the intermediate wall. The inlet pipe may be connected to a supply of disinfectant.

Typically the (or each) aperture within the access wall is a substantially circular aperture (eg a circular, elliptical or oval aperture). The glove port may be shaped to conform to the shape of the aperture so as to be fitted to the access wall at or near to the circumference thereof and coaxial therewith. Typically the glove port is a substantially cylindrical glove port. The substantially cylindrical glove port may be fitted to the front face of the access wall or at or near to the edge of the access wall bounding the substantially circular aperture in any convenient manner such as mechanically and/or adhesively (eg using conventional adhesives and/or fasteners such as threaded fasteners for example screws).

Generally speaking the flexible glove is composed of natural rubber (latex), Hypalon, neoprene, butyl or polyurethane rubbers. The flexible glove may be retained on the retaining portion in any conventional manner. The flexible glove may comprise a flexible sleeve terminating in a gloved end. Preferably in use the flexible sleeve extends beyond the operator's elbow to optimise maneuverability. The gloved end is typically composed of less flexible material than the flexible sleeve. For example, the gloved end may be composed of thicker polyurethane than that of the flexible sleeve (or alternatively of thicker PVC or other material). Typically the position and orientation of the flexible glove may be tailored to suit the particular operation to be conducted in the aseptic processing zone. For example, the flexible glove may be right-hand orientated or left-hand orientated as desired.

Where appropriate, a plurality of substantially circular apertures may be provided within the access wall of the multi-walled aseptic chamber. One or more additional walls of the multi-walled aseptic chamber may be provided with one or more substantially circular apertures. Each of these may be separately provided with a glove port and flexible glove.

The air quality in and around the aseptic processing zone may be controlled using forced ventilation and filtration. For example, the multi-walled aseptic chamber may be adapted to provide non-circulatory or recirculatory air flow in the aseptic processing zone. The air flow may be turbulent or unidirectional. The aseptic processing zone may be operable at a positive pressure.

The aseptic processing zone may be compartmentalised.

Viewed from a further aspect the present invention provides a multi-walled incubating enclosure as hereinbefore defined.

Viewed from a yet further aspect the present invention provides a multi-walled aseptic processing chamber as hereinbefore defined.

Viewed from a still further aspect the present invention provides a kit of parts comprising at least one multi-walled incubating enclosure as hereinbefore defined and a multi-walled aseptic processing chamber as hereinbefore defined, wherein the (or each) multi-walled incubating enclosure is dockable with the multi-walled aseptic processing chamber to define a transfer port between the incubation zone and the aseptic processing zone.

The present invention will now be described in a non-limitative sense with reference to the accompanying Figures in which:

FIGS. 4A and B are exploded sectional views of a part of the incubating enclosure (undocked);

FIGS. 6A and B are exploded sectional views of a part of the aseptic chamber (undocked)

Figure 1:
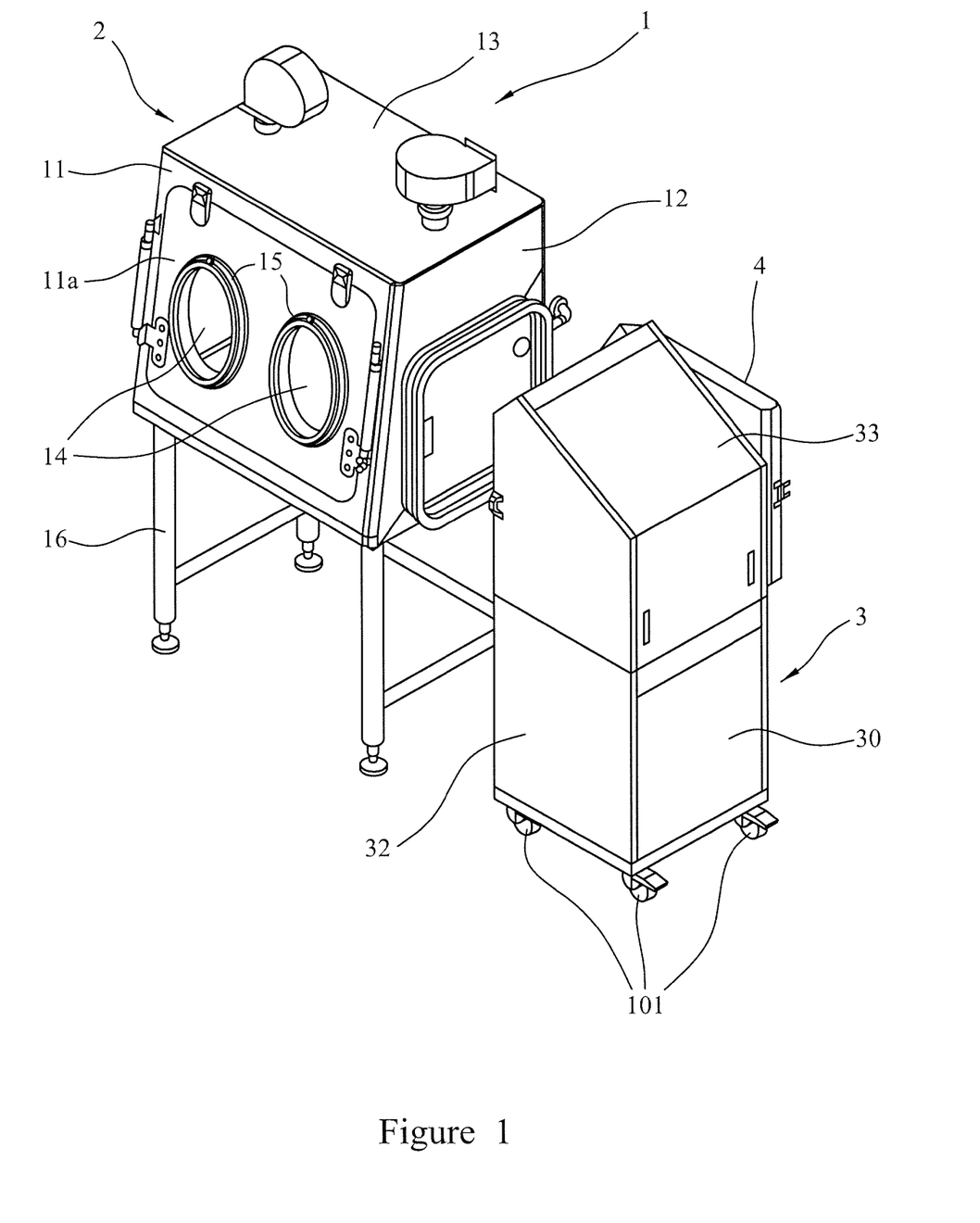
FIG. 1 illustrates an embodiment of the biological processing assembly of the invention with the aseptic chamber and incubating enclosure undocked.
Figure 2:
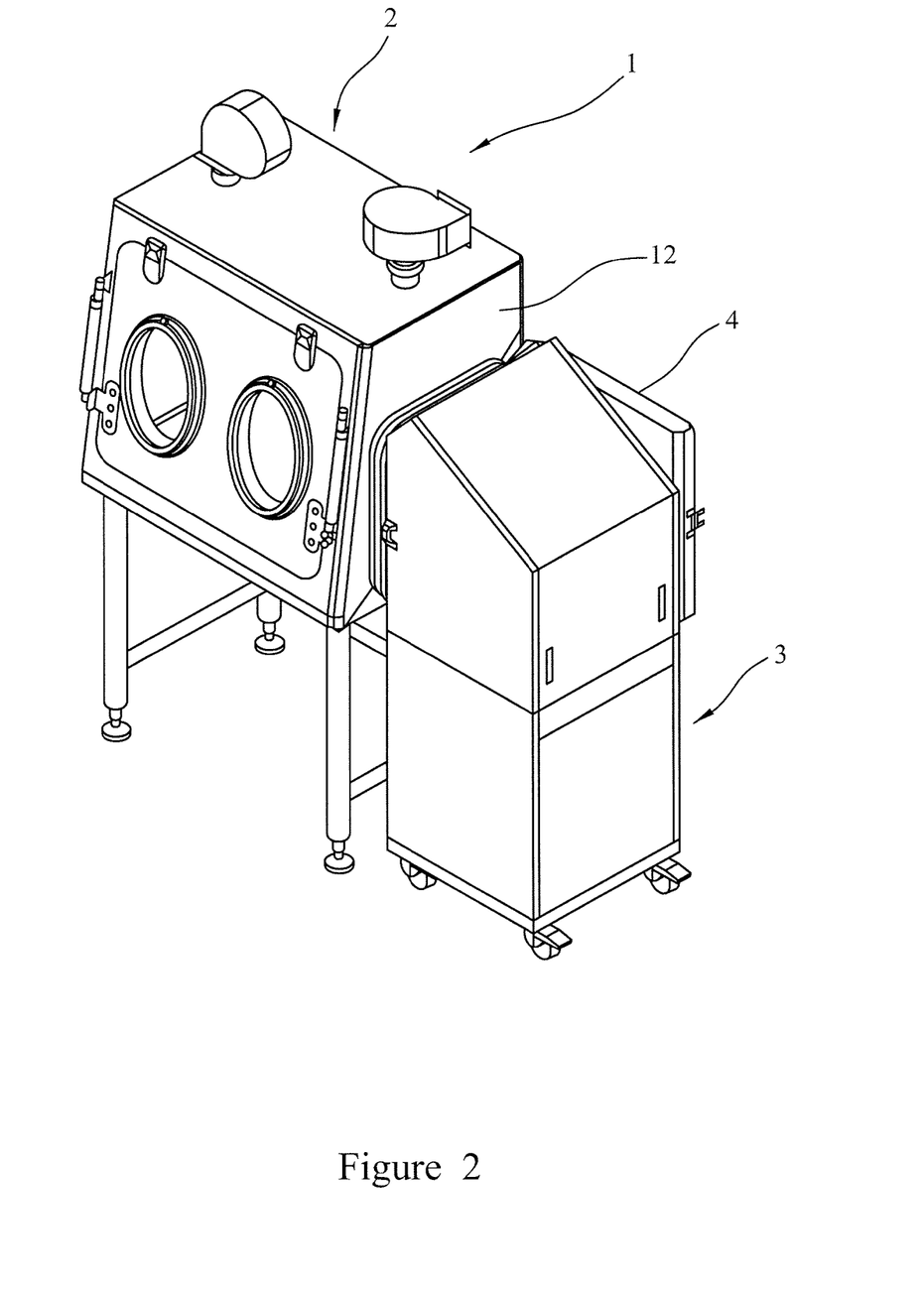
FIG. 2 illustrates the embodiment of the biological processing assembly of the invention with the aseptic chamber and incubating enclosure docked.
Figure 4:
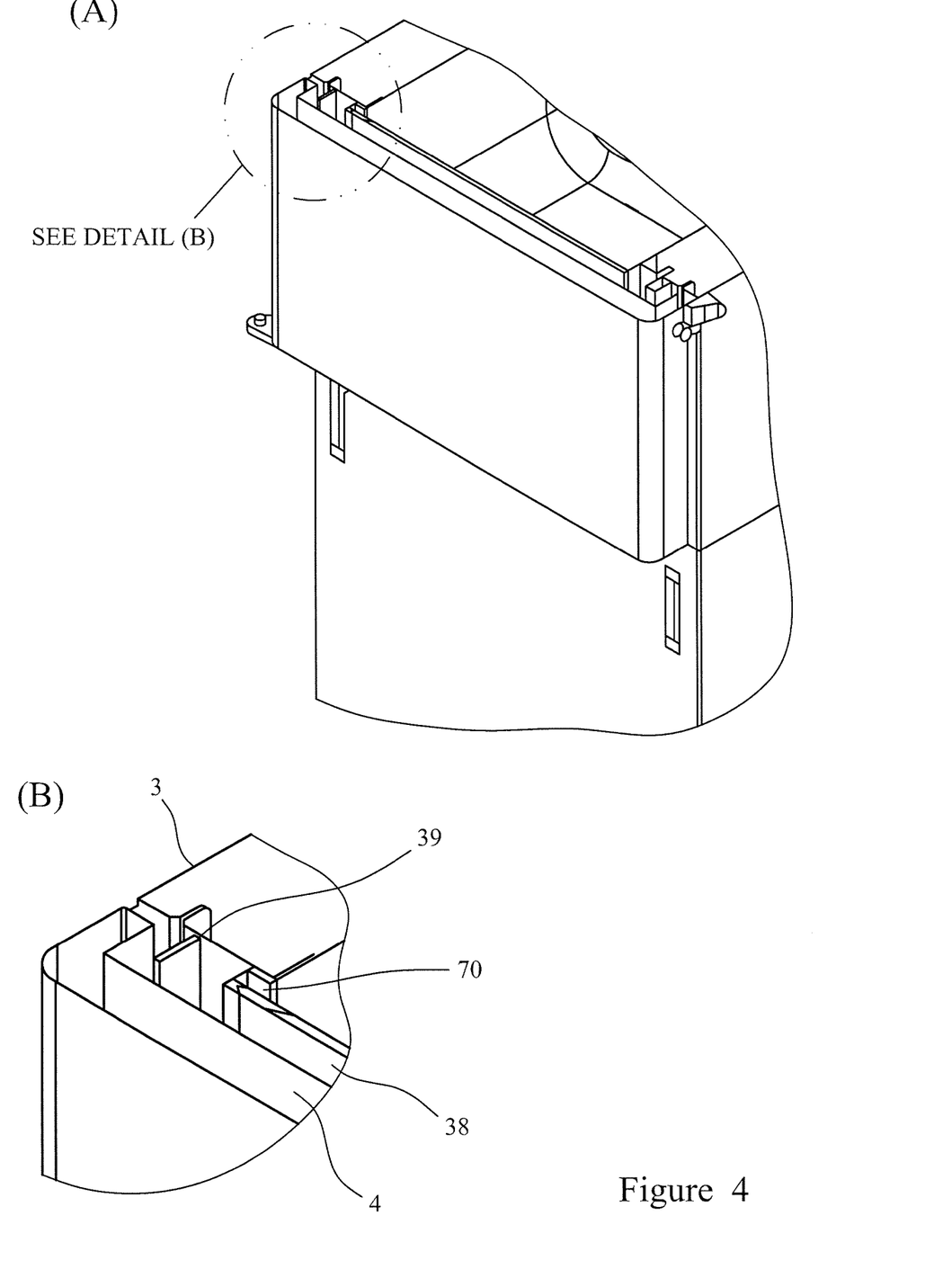
Figure 5:
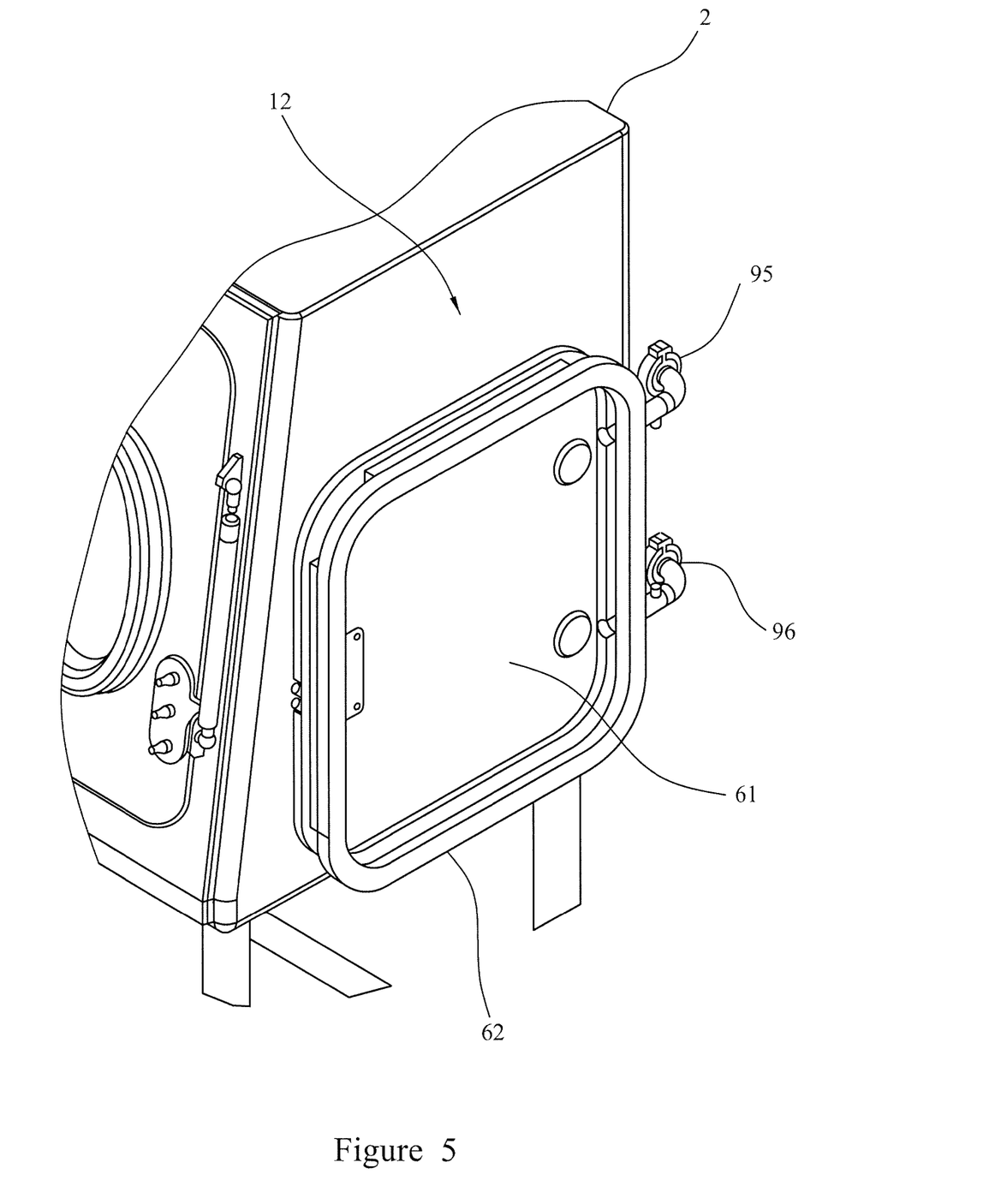
FIG. 5 is a view of a part of the aseptic chamber (undocked)

FIGS. 1 and 2 illustrate respectively an embodiment of the biological processing assembly of the invention 1 with an aseptic chamber 2 and an incubating enclosure 3 in an undocked and docked position respectively. An exterior door 4 mounted on a wall of the incubating enclosure 3 is closed when the aseptic chamber 2 and incubating enclosure 3 are undocked (see FIG. 4) and is opened for the purposes of docking. The aseptic chamber 2 encloses an aseptic processing zone and is equipped to carry out processing of biological entities. The incubating enclosure 3 encloses an incubation zone and is equipped to carry out incubation of biological entities.

The aseptic chamber 2 is multi-walled and adopts a substantially cuboidal configuration with a rear wall (hidden), a front wall 11, a basal wall (hidden), a first side wall 12, a second side wall (hidden) and an upper wall 13. The basal wall is equipped with a ground-bearing framework 16.

The front wall 11 is an access wall and takes the form of a framed transparent window 11a which includes a pair of apertures 14. A glove port 15 is fitted to the front wall 11 at the circumference of and coaxial with each aperture 14 and an exterior surface of the glove port 15 extends into a retaining portion which retains a flexible glove (omitted from the Figures for the purposes of clarity).

Figure 6:
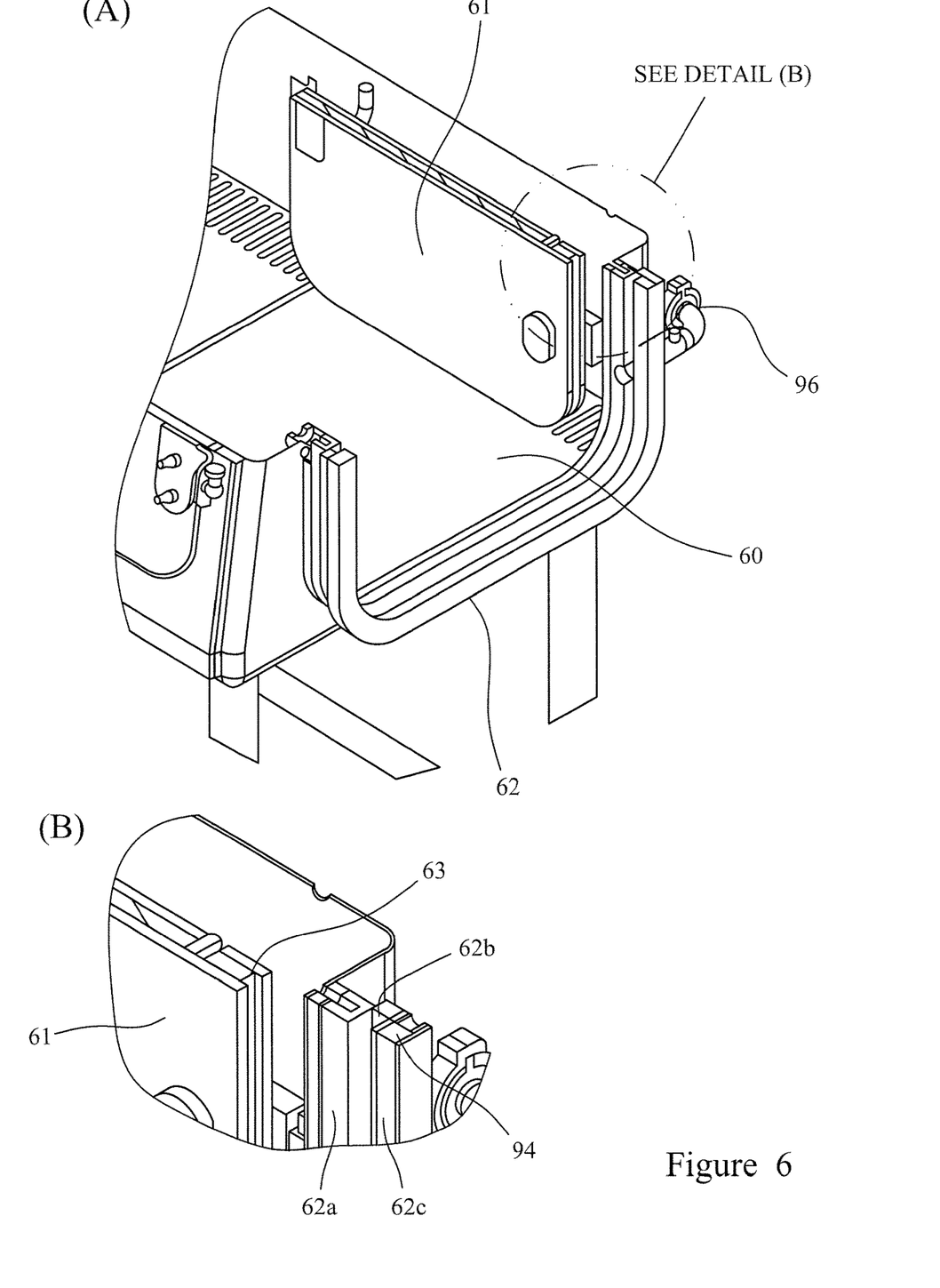

The first side wall 12 is a transfer wall which includes a transfer hatch 60 (see FIG. 6A) which is selectively closed by a transfer door 61 pivotally mounted on the first side wall 12. An outer circumferential edge of the transfer door 61 is recessed to encapsulate a first inflatable seal 63 (shown deflated in FIG. 6).

The lip of the transfer hatch 60 extends outwardly and radially into an innermost seat 62a of a stepped collar 62 which is engaged by the outer circumferential edge of the transfer door 61 so as to close the transfer hatch 60. A proximity switch (not shown) triggers inflation of the first inflatable seal 63 when the transfer hatch 60 is closed.

The innermost seat 62a of the stepped collar 62 extends outwardly and radially into an intermediate wall 62b. The intermediate wall 62b extends outwardly and radially into an annularly recessed seat 62c in which is mounted a second inflatable seal 94. The annularly recessed seat 62c of the stepped collar 62 is outermost. A proximity switch (not shown) triggers inflation of the second inflatable seal 94 when the aseptic chamber 2 and incubating enclosure 3 are docked.

An inlet pipe 95 and an outlet pipe 96 are connected to respective bores in the intermediate wall 62b of the stepped collar 62. The inlet pipe 95 is connected to a supply of a disinfectant.

The incubating enclosure 3 is multi-walled and adopts a substantially cuboidal configuration with a rear wall 30, a front wall 31, a basal wall (hidden), a first side wall 32, a second side wall (hidden) and an upper wall 33. The basal wall is equipped with wheels 101 so that the incubating enclosure 3 is mobile and can be propelled manually between an undocked position (FIG. 1) and a docked position (FIG. 2).

Figure 3:
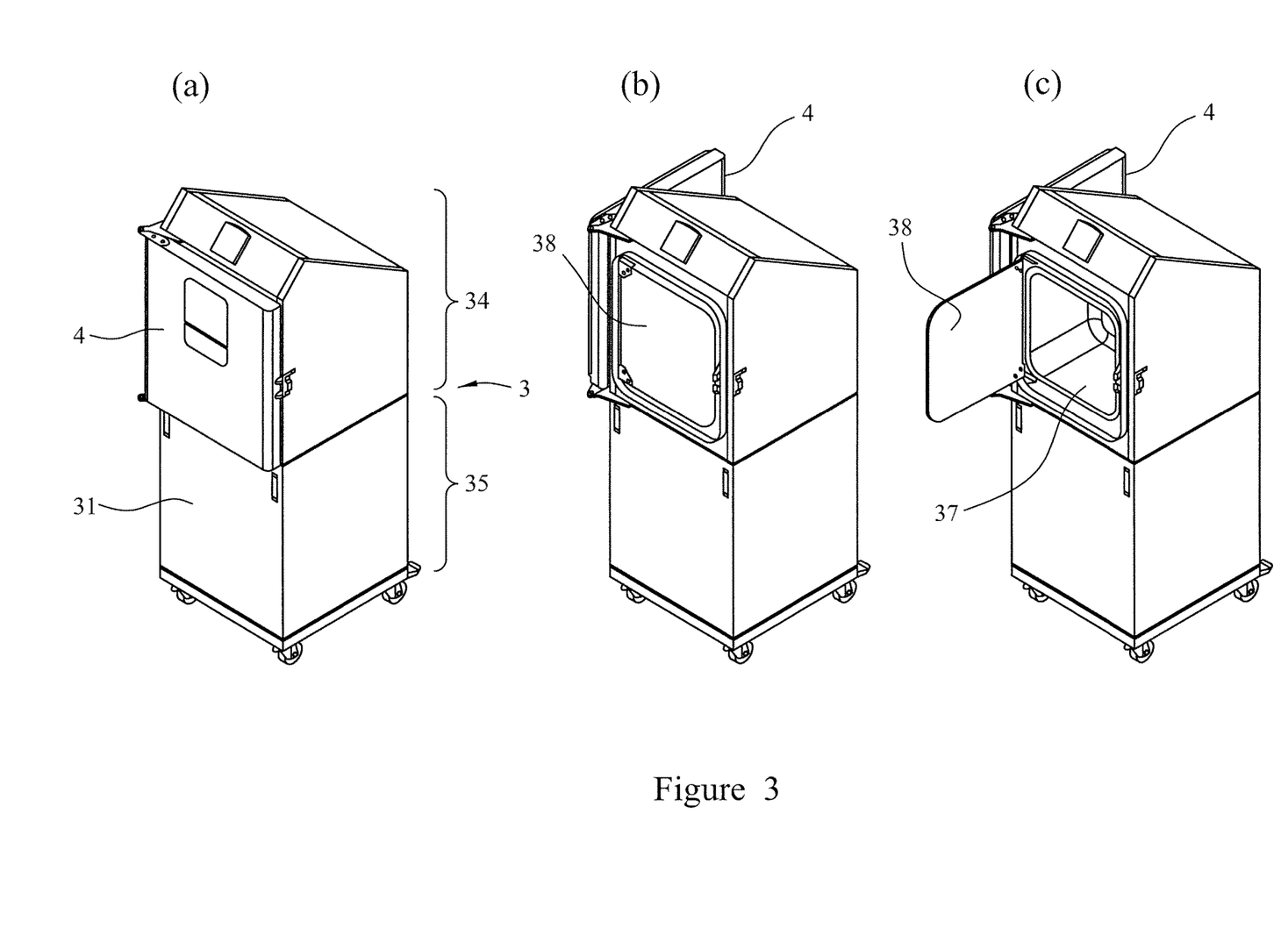
FIGS. 3a-c illustrate the incubating enclosure (undocked)

The incubating enclosure 3 is split into an upper compartment 34 and a lower compartment 35 (see FIG. 3). The front wall 31 is an outlet wall which includes an outlet hatch 37 in the upper compartment 34. A barrier door 38 is mounted pivotally on the front wall 31 to selectively open and close the outlet hatch 37.

FIGS. 4A and B are exploded sectional views of a part of the incubating enclosure 3 in the undocked position with the barrier door 38 and main door 4 closed. A docking spigot 39 extends outwardly from an exterior surface of the front wall 31 and skirts the outlet hatch 37 and barrier door 38. An inner seal 70 is mounted on the front wall 31 to provide a seal with the barrier door 38 when the outlet hatch 37 is closed.

Figure 7:
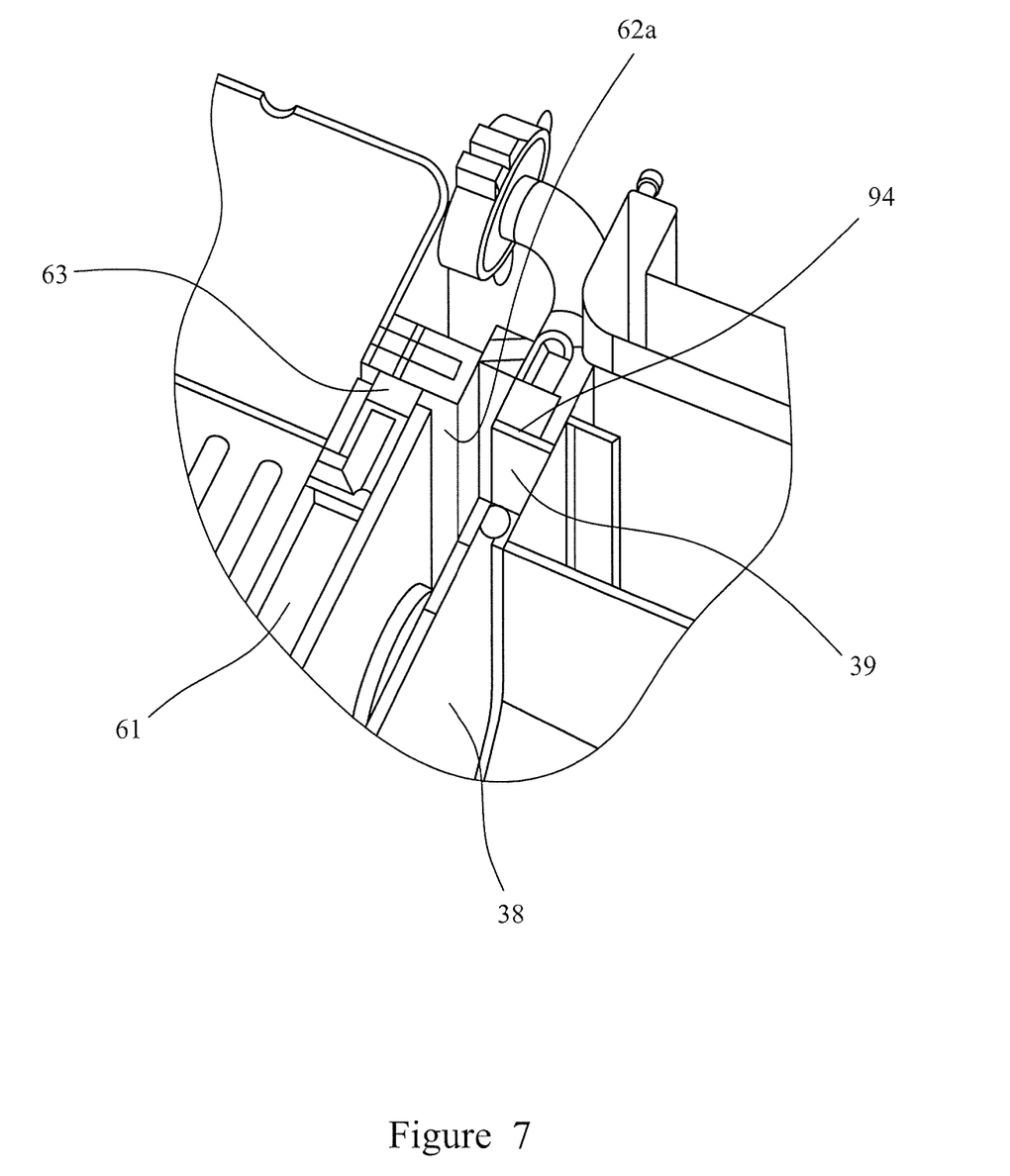
FIGS. 7 to 9 are exploded sectional views of a part of the incubating enclosure and the aseptic chamber (docked).
Figure 8:
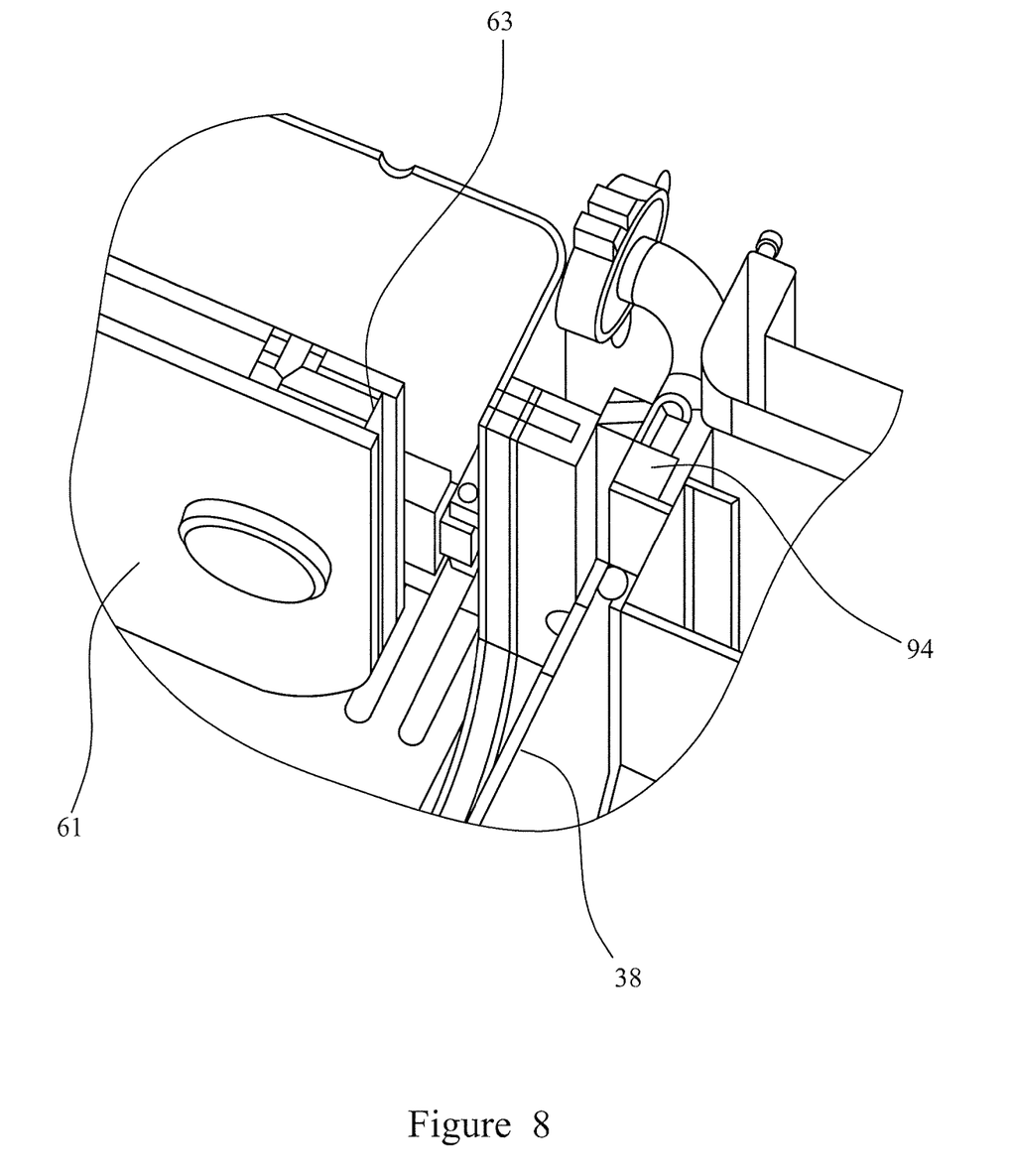
Figure 9:
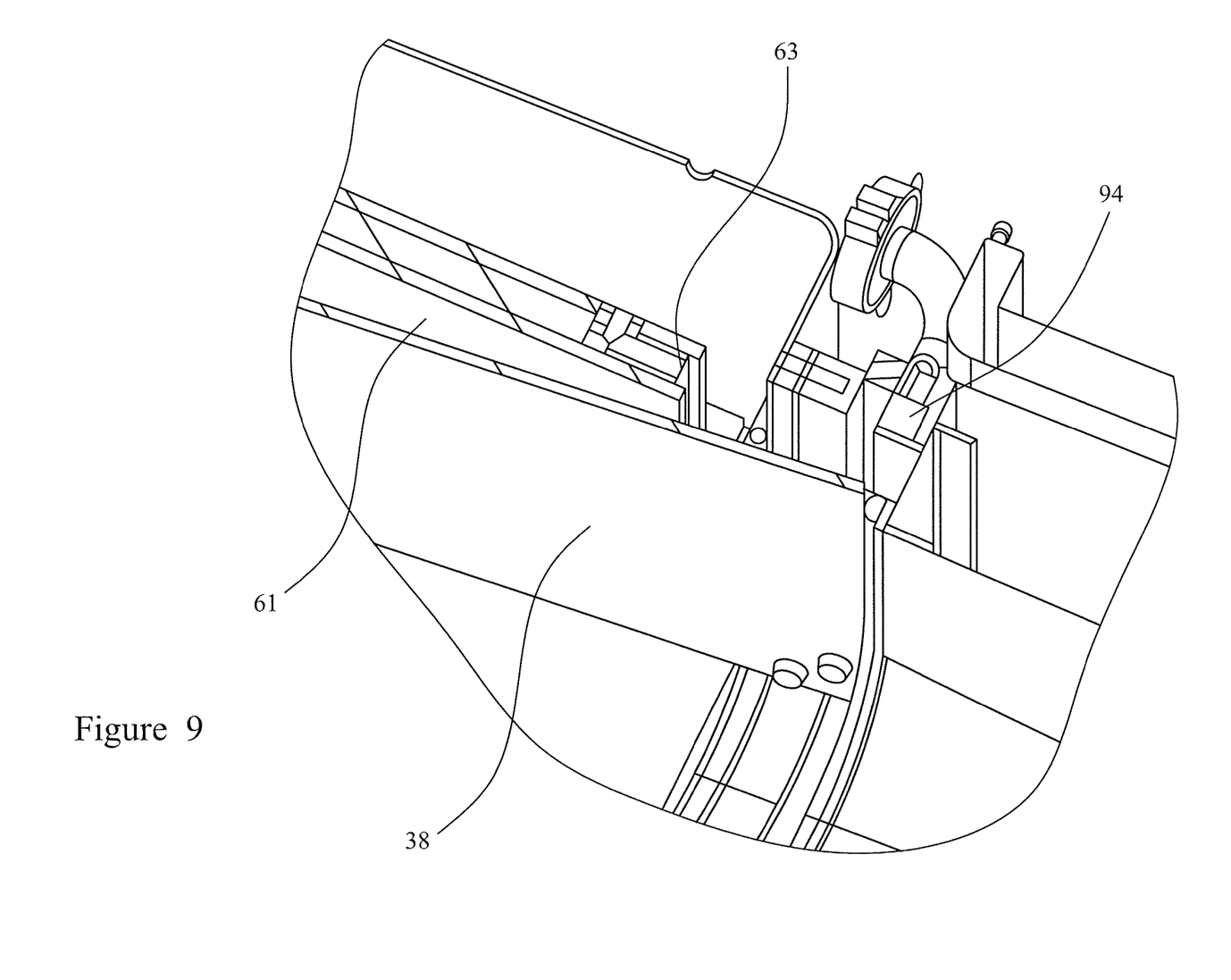

FIGS. 7 to 9 are exploded sectional views of a part of the incubating enclosure 3 and the aseptic chamber 2 in the docked position.

As shown in FIG. 7, the transfer door 61 is closed and the first inflatable seal 63 is inflated to form a seal between the transfer door 61 and the innermost seat 62a of the stepped collar 62. The barrier door 38 is closed and the second inflatable seal 94 is inflated to form a seal between the docking spigot 39 and the annularly recessed seat 62c of the stepped collar 62. In these circumstances, the transfer port between the incubation zone and the aseptic processing zone is substantially isolated. The inlet pipe 95 and the outlet pipe 96 serve to cycle the disinfectant through the transfer port until the transfer port is bio-decontaminated.

When the transfer port is bio-decontaminated, the operator uses the flexible glove to reach through the aperture 14 within the front wall 11 to pivot the transfer door 61 to disengage from the innermost seat 62a of the stepped collar 62. Thus as shown in FIG. 8, the transfer hatch 60 is open and the first inflatable seal 63 is deflated. In these circumstances, the operator has access from the aseptic processing zone to the bio-decontaminated transfer port.

With access from the aseptic processing zone to the bio-decontaminated transfer port, the operator uses the flexible glove to reach through the aperture 14 within the front wall 11 wall and the transfer hatch 60 within the first side wall 12 to pivot the barrier door 38 to open the outlet hatch 37. Thus as shown in FIG. 9, the transfer door 61 is open, the first inflatable seal 63 is deflated, the second inflatable seal 94 is inflated and the outlet hatch 37 is open. In these circumstances, the operator has access from the aseptic processing zone to the incubation zone through the bio-decontaminated transfer port to enable biological material to be transferred from the incubation zone to the aseptic processing zone where biological processing of the biological material can commence.

The invention claimed is:

1. A biological processing assembly comprising:
    a multi-walled aseptic chamber which encloses an aseptic processing zone beyond an access wall thereof for processing biological material;
    an aperture within the access wall;
    a glove port fitted to the access wall at or near to the circumference of and coaxial with the aperture, wherein an exterior surface of the glove port extends into a retaining portion;
    a flexible glove retained on the retaining portion of the glove port, wherein the flexible glove is adapted or adaptable to permit an operator outside the aseptic processing zone to reach through the aperture within the access wall to access the aseptic processing zone and beyond;

a transfer hatch within a transfer wall of the multi-walled aseptic chamber, wherein a lip of the transfer hatch extends radially and outwardly into an innermost seat of a stepped collar, the innermost seat of the stepped collar extends outwardly and radially into an intermediate wall, and the intermediate wall extends outwardly and radially into an annularly recessed seat of the stepped collar;

a transfer door mounted pivotally on the transfer wall of the multi-walled aseptic chamber, wherein in use the operator outside the aseptic processing zone reaches through the aperture within the access wall to pivot the transfer door to engage an outer circumferential edge of the transfer door with the innermost seat of the stepped collar so as to close the transfer hatch or to pivot the transfer door to disengage from the innermost seat of the stepped collar so as to open the transfer hatch;

a multi-walled incubating enclosure which encloses an incubation zone for the biological material;

an outlet hatch within an outlet wall of the multi-walled incubating enclosure;

a barrier door mounted pivotally on the outlet wall of the multi-walled incubating enclosure, wherein in use the operator outside the aseptic processing zone reaches through the aperture within the access wall and the transfer hatch within the transfer wall to pivot the barrier door to open or close the outlet hatch;

a docking spigot extending outwardly from an exterior surface of the outlet wall, wherein the docking spigot skirts the outlet hatch and is dockable or docked with the annularly recessed seat of the stepped collar to define a transfer port between the incubation zone and the aseptic processing zone;

a first seal mounted between the transfer door and stepped collar;

a second seal mounted between the docking spigot and stepped collar, wherein when the transfer door and barrier door are closed the transfer port is substantially isolated; and a disinfectant delivery device fitted to the stepped collar whereby in use to deliver disinfectant to the transfer port.

2. The biological processing assembly as claimed in claim 1 further comprising a second aperture within the access wall and a second glove port fitted to the access wall at or near to the circumference of and coaxial with the second aperture, wherein an exterior surface of the second glove port extends into a retaining portion and a second flexible glove is retained on the retaining portion of the second glove port, wherein the second flexible glove is adapted or adaptable to permit an operator outside the aseptic processing zone to reach through the second aperture within the access wall to access the aseptic processing zone.

3. The biological processing assembly as claimed in claim 1 wherein the multi-walled incubating enclosure is adapted for manual ground-bearing propulsion.

4. The biological processing assembly as claimed in claim 3 wherein the multi-walled incubating enclosure is wheeled.

5. The biological processing assembly as claimed in claim 1 wherein in use an outer circumferential edge of the transfer door engages the innermost seat of the stepped collar so as to close the transfer hatch and disengages from the innermost seat of the stepped collar so as to open the transfer hatch.

6. The biological processing assembly as claimed in claim 1 wherein the second seal is mounted in the annularly recessed seat of the stepped collar.

7. The biological processing assembly as claimed in claim 1 wherein the first seal is mounted in a recess in at least a part of the outer circumferential edge of the transfer door.

8. The biological processing assembly as claimed in claim 1 wherein the first seal is a first inflatable seal and the second seal is a second inflatable seal, wherein when the transfer door and barrier door are closed and the first inflatable seal and second inflatable seal are inflated the transfer port is substantially isolated.

9. The biological processing assembly as claimed in claim 1 further comprising an inner seal mounted between the barrier door and the outlet wall.

10. The biological processing assembly as claimed in claim 1 wherein the disinfectant delivery device comprises an inlet pipe connected to a first bore in the stepped collar and an outlet pipe connected to a second bore in the stepped collar.

* * * * *